United States Patent [19]

Ludick

[11] Plant 5,034

[45] Apr. 12, 1983

[54] HIBISCUS PLANT

[76] Inventor: Roberta J. Ludick, 13095 NE. 2nd Ave., North Miami, Fla. 33161

[21] Appl. No.: 310,070

[22] Filed: Dec. 21, 1981

[51] Int. Cl.[3] ..... A01H 5/00

[52] U.S. Cl. ..... Plt./54

[58] Field of Search ..... Plt./54

*Primary Examiner*—Robert E. Bagwill

[57] ABSTRACT

A new distinct variety of hibiscus plant, of the *Rosa-sinensis* species, having long-lasting, double blooms.

3 Drawing Figures

The plant is characterized as to novelty by its vigorous, upright habit of growth, its crisp green foliage, and its brilliant, long-lasting flowers. A particular feature of the new variety is that the flowers will last for two days, except in very hot weather. Most hibiscus flowers last for one day only.

A plant and flower of the new variety are shown in full color in the accompanying illustration.

A detailed description of the new variety follows, and to facilitate identification of the important colors, the color terminology adopted by The British Horticultural Colour Charts has been followed. (Reference is to "Horticultural Colour Charts" issued by the British Color Council in two volumes, in collaboration with The Royal Horticultural Society, copyright by Robert F. Wilson, published 1938–1941).

PLANT CHARACTERISTICS

Name: "Joanne Boulin".

Parentage: Seedling resulting from definite breeding efforts.

*Seed parent.*—Charles September.

Growth: The plant is of vigorous upright growth, well-clothed with foliage. The ultimate height of the plant is not known, but under normal conditions it should reach a height of 6 to 8 feet, with a spread of 3 to 4 feet.

Branches: New branch growth is a light green (Scheeles Green 860) changing to a light brown as it matures. Bark is slightly rough.

Growing habit: Branching starts just above ground level and has a tendency to be ascending.

Foliage: The leaves are of good substance and are glossy.

*Shape.*—The leaves are best described as being broadly cordate, with the margin crenate. The apex of the leaf is acute, the base truncate.

*Color.*—The upper surface of the leaf is Spinach Green o960; the underside is Scheeles Green 860.

*Size.*—Leaves are from 3¼ to 4¼ inches wide, and from 3¾ to 5 inches long. Petiole is 1¾ inches long.

*Arrangement.*—Leaves are alternate on the stems.

*Veins.*—The underside of each leaf has prominent veins, extending from the base of the leaf. Veins are slightly darker in color than the underside of the leaf.

Flower: The plant blooms in great abundance all year in southern Florida, with lighter bloom in summer months.

*Form.*—Double — varies from 6½ to 7½ inches across the flower.

*Petals.*—Petals are eight to ten in number and are overlapping and very ruffled.

*Color.*—The base of the petal is Spinel Red, R.H.S. 0023, shading to Spinel Red 0023/1 to Spinel Red 0023/3, three-fourths of the way on each petal. Has an outside ring, about 1 inch of Chrome Yellow R.H.S. 6053 - B & C. Back of petals is shaded Spinel Red 0023/3 to Chrome Yellow 6053-D and splash of Primrose Yellow 601-2-C.

*Veins.*—Veins are Spinel Red, R.H.S. 0023.

*Stigma pads.*—Stigma pads are Sulphur Yellow R.H.S. ⅓-D with ring of Spanish Orange R.H.S. 010-A.

*Style.*—Style is 2¾ long and Spinel Red 0023/1 to Spinel Red 0023/3 to white.

I claim:

1. A new and distinct variety of hibiscus plant, of *Rosa-sinensis* species, substantially as herein described and illustrated, and characterized particularly as to novelty by its vigorous, upright habit of growth, its crisp green foliage, and its brilliant, long-lasting flowers.

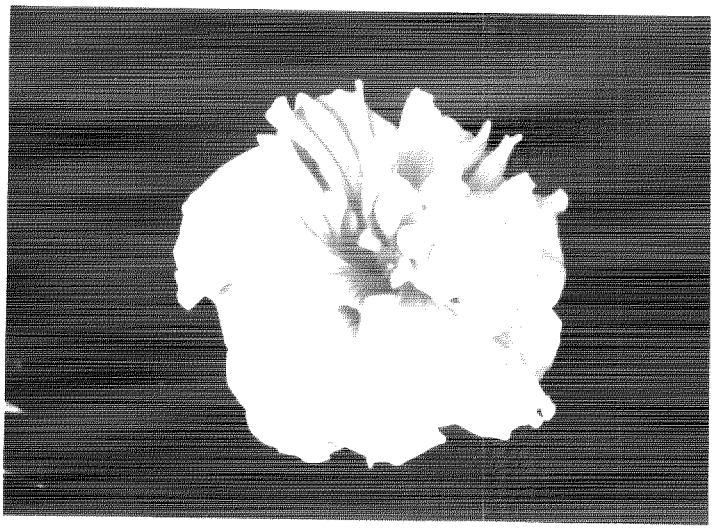
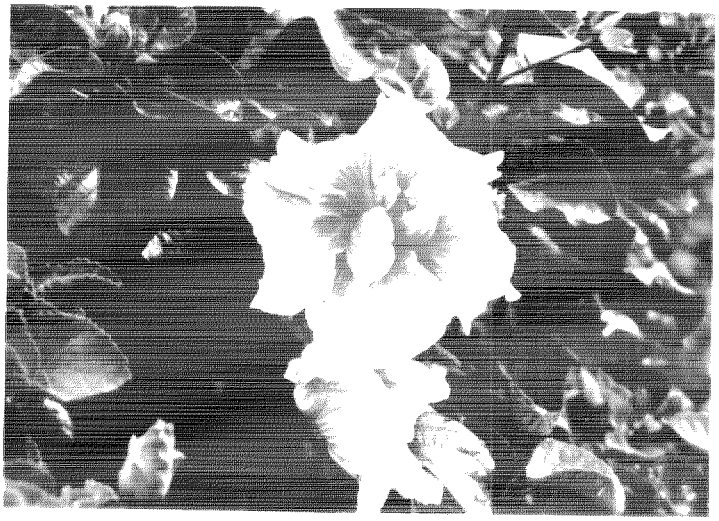
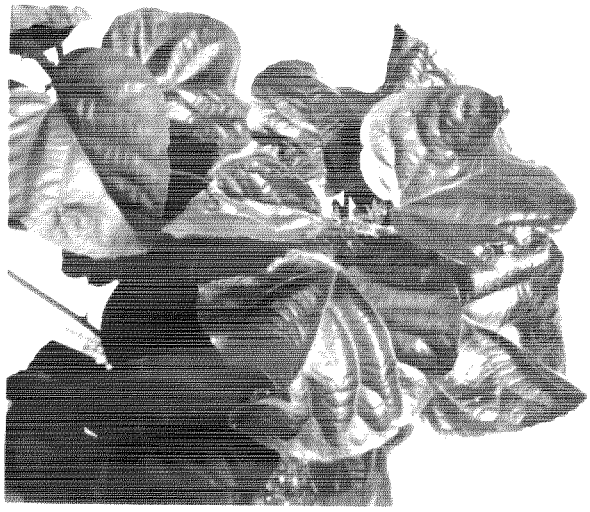

* * * * *